United States Patent [19]

Izumi

[11] Patent Number: 5,743,862
[45] Date of Patent: Apr. 28, 1998

[54] ULTRASONIC MEDICAL TREATMENT APPARATUS

[75] Inventor: Mamoru Izumi, Tokyo, Japan

[73] Assignee: Kabushiki Kaisha Toshiba, Kawasaki, Japan

[21] Appl. No.: 529,072

[22] Filed: Sep. 15, 1995

[30] Foreign Application Priority Data

Sep. 19, 1994 [JP] Japan .................. 6-222771
Mar. 14, 1995 [JP] Japan .................. 7-053804

[51] Int. Cl.⁶ ........................................... A61B 17/22
[52] U.S. Cl. .................................. 601/2; 310/334
[58] Field of Search ............... 601/2, 4; 128/660.03; 310/334, 335, 320

[56] References Cited

U.S. PATENT DOCUMENTS

| | | | |
|---|---|---|---|
| 3,904,896 | 9/1975 | Guntersdorfer | 310/8.1 |
| 4,276,491 | 6/1981 | Daniel | 128/662.04 |
| 4,907,573 | 3/1990 | Nagasaki | 601/4 |
| 4,963,282 | 10/1990 | Bui et al. | 310/334 |
| 5,070,486 | 12/1991 | Boucher | 310/334 |
| 5,164,920 | 11/1992 | Bast et al. | 601/2 |
| 5,295,487 | 3/1994 | Saitoh et al. | 128/662.03 |
| 5,316,000 | 5/1994 | Chapelon et al. | |
| 5,438,998 | 8/1995 | Hanafy | 128/662.03 |
| 5,526,815 | 6/1996 | Grant et al. | 601/4 |

OTHER PUBLICATIONS

Ultrasound in Medicine and Biology, vol. 21, No. 3, pp. 365–377, 1995, "Electronic Beam Steering of Shock Waves"; Cathignol et al. 1994.

*Primary Examiner*—Brian L. Casler
*Attorney, Agent, or Firm*—Oblon, Spivak, McClelland, Maier & Neustadt, P.C.

[57] ABSTRACT

An applicator includes a concave piezoelectric oscillator. The concave piezoelectric oscillator comprises a plurality of piezoelectric oscillation plates having equal areas. Each piezoelectric oscillation plate comprises a plurality of piezoelectric oscillator elements. Each piezoelectric oscillator element has a higher resonance frequency in the lateral direction thereof than in the thickness direction thereof.

18 Claims, 8 Drawing Sheets

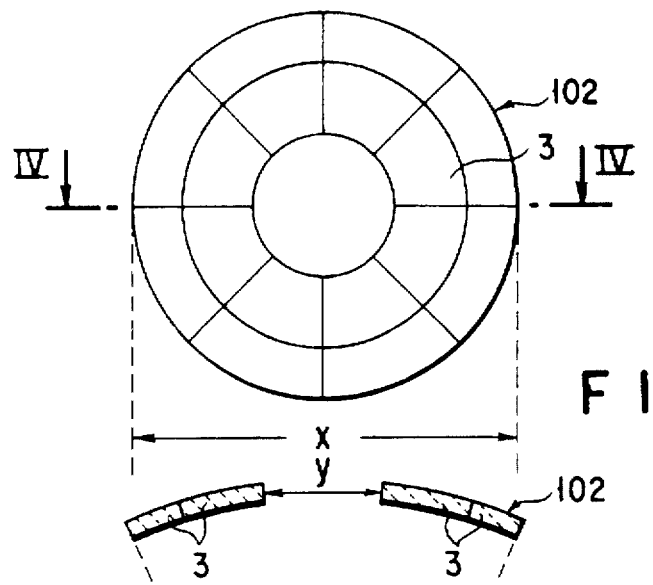
FIG. 3
FIG. 4
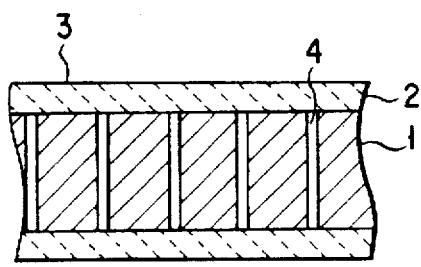
FIG. 5
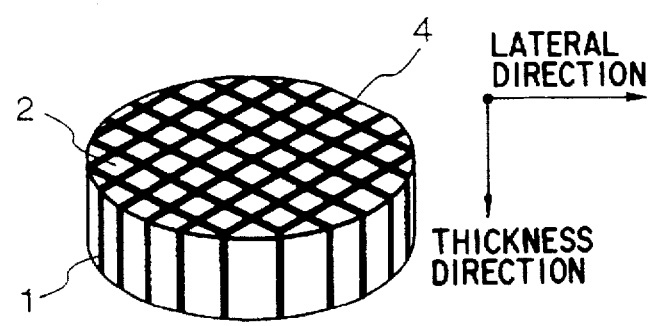
FIG. 6

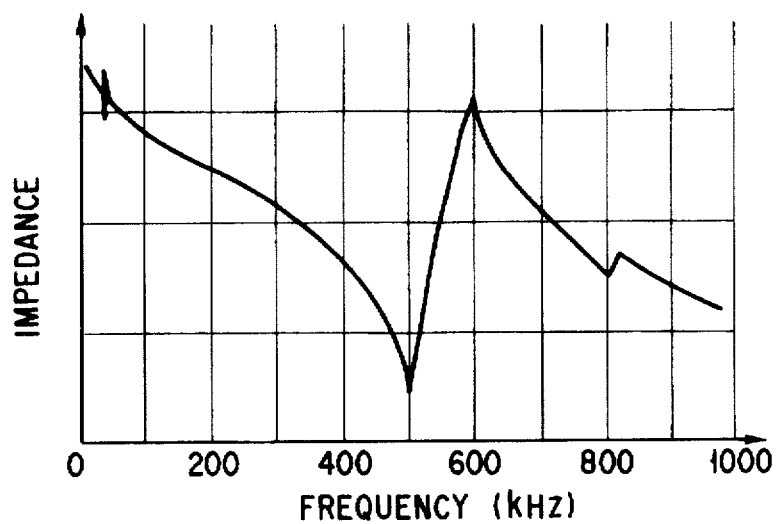
F I G. 7
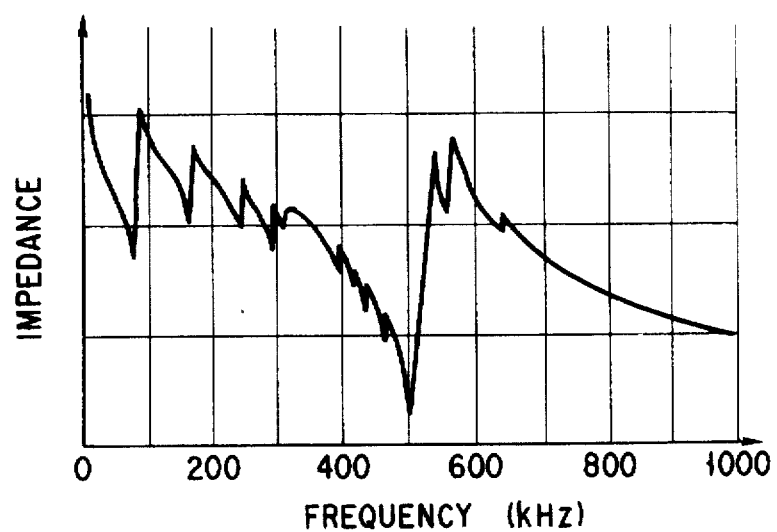
F I G. 8
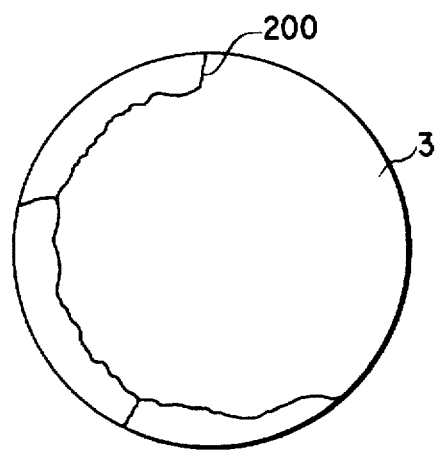
F I G. 9

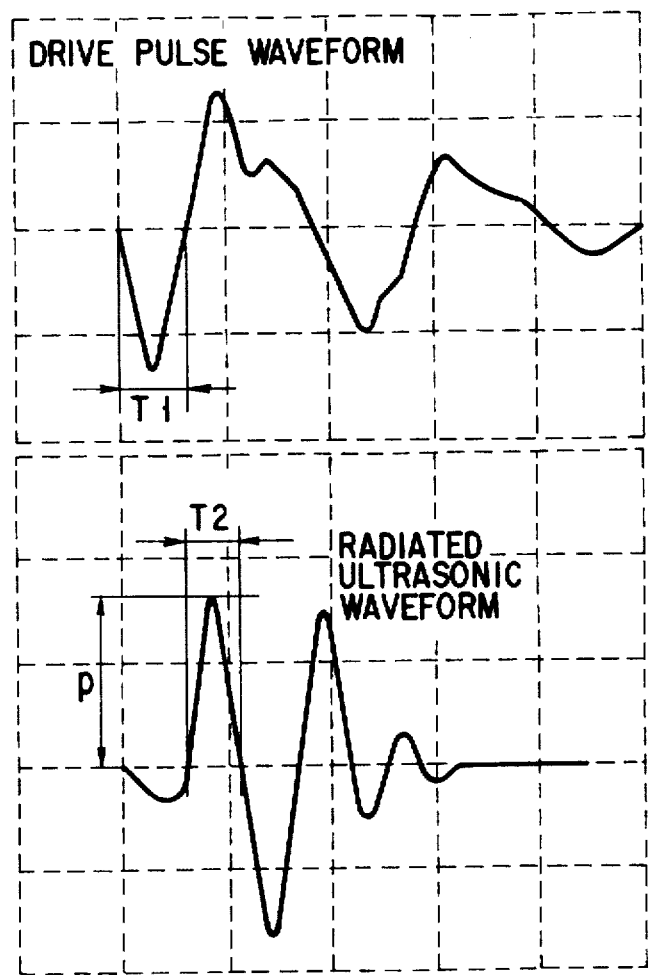
FIG. 12A
FIG. 12B
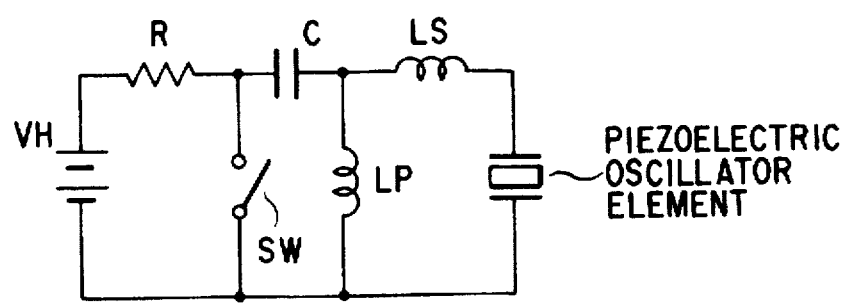
FIG. 13

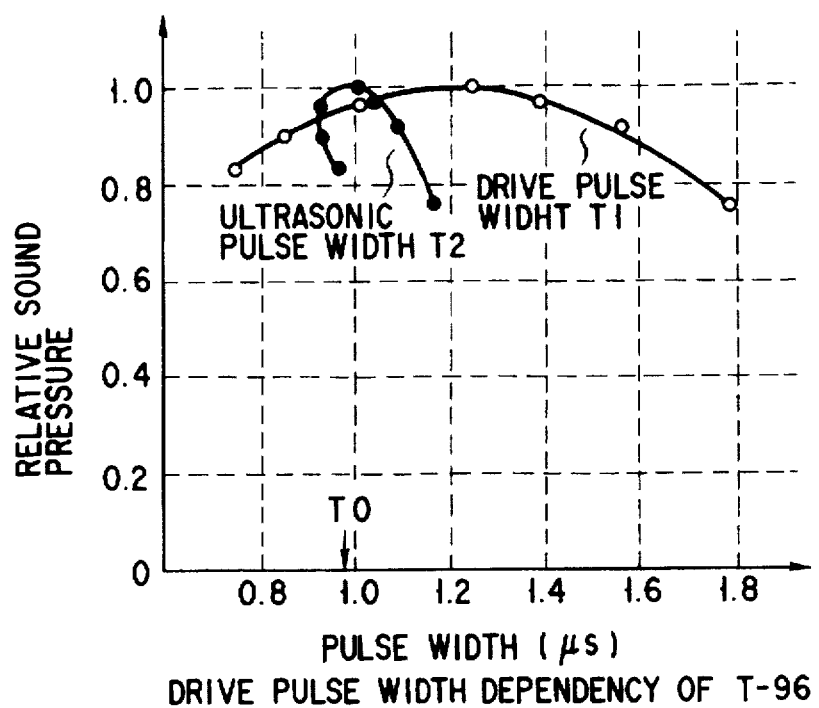
DRIVE PULSE WIDTH DEPENDENCY OF T-96
F I G. 14
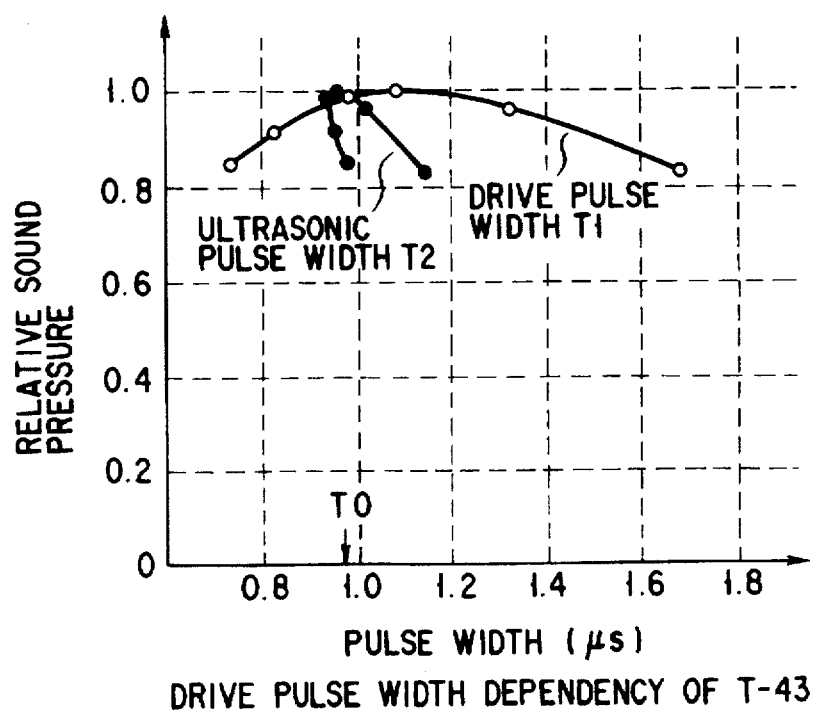
DRIVE PULSE WIDTH DEPENDENCY OF T-43
F I G. 15

DRIVE PULSE WIDTH DEPENDENCY OF T-99

DRIVE PULSE WIDTH DEPENDENCY OF C-7

ULTRASONIC MEDICAL TREATMENT APPARATUS

BACKGROUND OF THE INVENTION

1. Field of the Invention

The present invention relates to an ultrasonic medical treatment apparatus such as a lithotrity apparatus for breaking culculi by shock waves produced on the basis of strong ultrasonic waves.

2. Description of the Related Art

An ultrasonic medical treatment apparatus such as a lithotrity apparatus generates strong ultrasonic waves from an applicator. A piezoelectric oscillator (concave oscillator) mounted on a frame of the applicator needs to have a diameter of about 300 mm in order to produce energy necessary for breaking culculi. In addition, in order to converge radiated ultrasonic waves, the piezoelectric oscillator is designed to have a substantial spherical-shell shape (concave shape).

It is difficult to manufacture such a large-sized piezoelectric oscillator as one body of piezoelectric ceramic or single crystal. Thus, a plurality of piezoelectric oscillation plates are individually manufactured, and these are combined to constitute a large-sized piezoelectric oscillator. Specifically, the piezoelectric oscillation plate comprises a great number of small piezoelectric oscillator elements, and the substantially spherical-shell-shaped (concave) oscillator comprises the piezoelectric oscillation plates.

In order to increase the shock wave energy at the focal point in the above ultrasonic medical treatment apparatus, it is necessary to increase an input energy to the piezoelectric oscillator. The input energy to the capacitance load such as the piezoelectric oscillator is expressed by $CV^2/2$, where C=load capacitance and V=applied voltage. The input energy is proportional to the square of the applied voltage. Accordingly, it is understood that in order to efficiently increase the output energy, the applied voltage must be increased.

However, in a conventional ultrasonic medical treatment apparatus, if a high-voltage pulse exceeding, e.g. 500 V/mm, is applied, fatigue failure occurs in the piezoelectric oscillation plate and, accordingly, the piezoelectric oscillator. Thus, if high-voltage pulses are applied repeatedly, the shock wave energy decreases. In the worst case, the generation of shock waves is disabled.

On the other hand, the conventional ultrasonic medical treatment apparatus has the following problem relating to pulse waveforms of drive voltage. That is, it is desirable that the piezoelectric oscillation plates of the piezoelectric oscillator of the applicator have substantially equal areas in order to equalize electrical loads on drive circuits of the respective piezoelectric oscillation plates. A central portion of the applicator, on which the piezoelectric oscillation plates are mounted, is provided with a hole for insertion of an ultrasonic probe of a ultrasonic diagnosis apparatus, thereby to effect alignment and acquire ultrasonic tomographic images for observation. An ultrasonic radiation surface of the piezoelectric oscillator is provided with a resin layer for achieving acoustic matching with water or propagation medium, waterproof, and electrical insulation.

When a voltage is applied to electrodes provided on both surfaces of each piezoelectric oscillation plate of the piezoelectric oscillator, the oscillation plate extends and contracts in the thickness direction thereof and radiates ultrasonic waves to the propagation medium. The radiated ultrasonic waves with large amplitudes are converted to shock waves, as shown in FIGS. 1A and 1B, by a non-linear phenomenon occurring while the ultrasonic waves propagate through the water and human body. As is shown in FIGS. 1A and 1B, several ultrasonic pulses of sine waves are radiated from the oscillator, as observed at point A. While the ultrasonic waves propagate through the water towards focal point C, the amplitude of the ultrasonic waves increases and the wave fronts rise in a sawtooth shape, as observed at point B. At focal point C, the wave front of the top wave alone is left and a shock wave is produced.

It is desirable that the shock wave have a single waveform and also that the ultrasonic wave radiated from the piezoelectric oscillation plate have a single waveform. The oscillator is driven by a drive pulse matched with a resonance frequency of the piezoelectric oscillation plates in order to increase the sound pressure amplitude of the radiated ultrasonic wave.

As described above, in the conventional ultrasonic medical treatment apparatus, if a high-voltage pulse is applied in order to increase a breaking power, fatigue failure occurs in the piezoelectric oscillation plate and consequently the generation of shock waves is disabled. In consideration of the application to a lithotrity apparatus, it is required that the shock wave energy be great. However, the increase in drive pulse voltage is limited. Therefore, an efficient shock wave generating source is desired.

SUMMARY OF THE INVENTION

An object of the present invention is to provide an ultrasonic medical treatment apparatus with a high breaking power and high reliability.

Another object of the invention is to provide a shock wave generating apparatus capable of generating a shock wave with high shock wave energy.

In order to achieve the above objects, according to the present invention, there is provided an ultrasonic medical treatment apparatus comprising:

a plurality of piezoelectric oscillator elements each having a higher resonance frequency in the lateral direction thereof than in the thickness direction thereof; and a drive unit for supplying a drive voltage to each of the piezoelectric oscillator elements.

According to this invention, there is also provided an ultrasonic medical treatment apparatus comprising;

a piezoelectric oscillator; and a drive unit for supplying to the piezoelectric oscillator a drive voltage having a pulse width ($T_1$) of a first negative amplitude, which is greater than a pulse width ($T_0$) corresponding to the resonance frequency of the piezoelectric oscillator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 3 is a schematic plan view showing an example of a piezoelectric oscillator of the ultrasonic medical treatment apparatus according to the invention;

FIG. 4 is a cross-sectional view taken along line IV—IV in FIG. 3;

FIG. 5 is an enlarged view of a part of FIG. 4;

FIG. 6 is a schematic perspective view of a first example of a piezoelectric oscillation plate of the present invention;

FIG. 7 is a graph showing resonance characteristics of the piezoelectric oscillation plate according to the invention;

FIG. 8 is a graph showing resonance characteristics of a conventional piezoelectric oscillator;

FIG. 9 shows cracks in the conventional piezoelectric oscillator;

FIGS. 12A and 12B show a drive pulse waveform and an ultrasonic waveform in the present invention;

FIG. 13 shows an equivalent circuit of the piezoelectric oscillation plate (piezoelectric oscillator) ad drive power supply;

FIGS. 14 to 17 are graphs showing the relationships between a relative sound pressure and a pulse width.

DETAILED DESCRIPTION OF THE PREFERRED EMBODIMENTS

Figure 2:
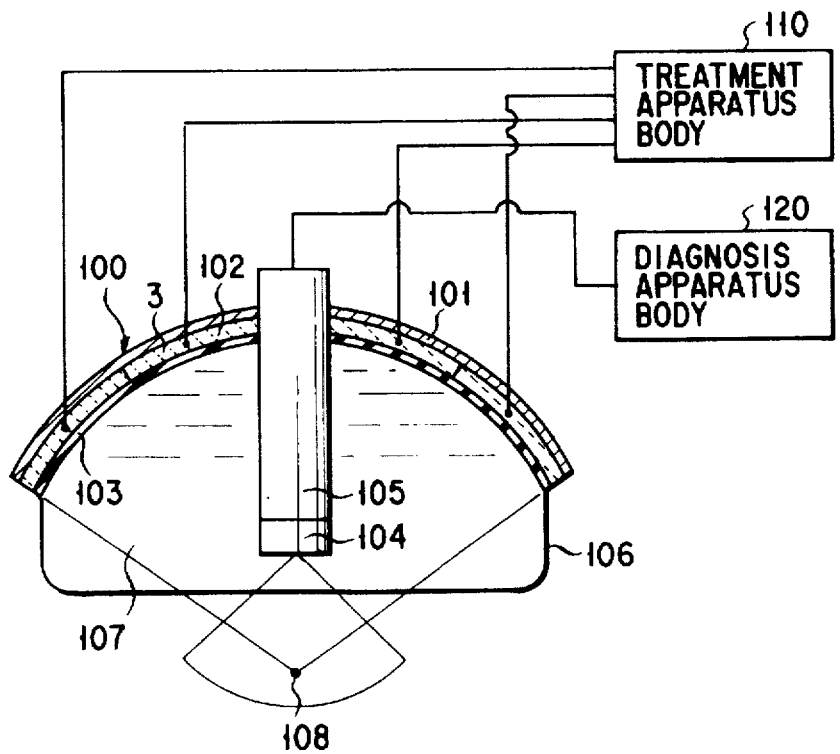
FIG. 2 schematically shows an ultrasonic medical treatment apparatus according to the present invention.

An ultrasonic medical treatment apparatus according to an embodiment of the present invention will now be generally described with reference to FIG. 2. The ultrasonic medical treatment apparatus according to this embodiment, as shown in FIG. 2, generally comprises an applicator 100, a treatment apparatus body 110 and a diagnosis apparatus body 120. In the applicator 100, a plurality of piezoelectric oscillation plates 3 are arranged on a concave-side surface of a concave frame 101 having a hole in a central portion thereof. The piezoelectric oscillation plates 3 constitute a concave piezoelectric oscillator 102. An ultrasonic radiation surface of the concave piezoelectric oscillator 102 is provided with a resin layer 103 for achieving acoustic matching with water or propagation medium, waterproof, and electrical insulation. The diameter of the piezoelectric oscillator 102 is about 300 mm. Each of the piezoelectric oscillation plates 3 is supplied with a drive voltage from a drive power supply included in the treatment apparatus body 110. An ultrasonic probe rod 105 having an ultrasonic probe 104 at a tip portion thereof is situated vertically movably in the hole in the concave frame 101. The ultrasonic probe 104 of the ultrasonic probe rod 105 is connected to the diagnosis apparatus body 120. The concave piezoelectric oscillator 102 is provided with a bag 106 in which water 107 is contained.

In the above structure, when the drive voltage is applied from the drive power supply included in the treatment apparatus body 110 to the respective piezoelectric oscillation plates 3, a shock wave occurs at focal point 108. In addition, a tomographic image of a region including the focal point 108 can be obtained by electronically scanning the ultrasonic probe 104 by the diagnosis apparatus body 120.

With reference to FIGS. 3 to 5, an example of the concave piezoelectric oscillator 102 of the ultrasonic medical treatment apparatus of the present invention will now be described in detail. As is shown in FIG. 5, the piezoelectric oscillation plate 3 comprises a plurality of piezoelectric oscillator elements each comprising opposed electrodes 2 (common electrodes in FIG. 5) and a piezoelectric body 1. The piezoelectric oscillator elements are arranged with gaps 4. A plurality of piezoelectric oscillation plates 3 are combined in a substantial spherical shell shape, thereby constituting the concave piezoelectric oscillator 102. Ultrasonic waves produced by applying electric pulses to the piezoelectric oscillator elements of the piezoelectric oscillation plates 3 are converged and converted to shock waves near the focal point, thereby breaking calculi.

The resonance frequency in the lateral direction of the piezoelectric oscillation plates 3 of the piezoelectric oscillator 102 and the piezoelectric oscillator elements of the piezoelectric oscillation plates 3, i.e. the resonance frequency in the tangential direction of the substantial spherical shell, is set to be higher than the resonance frequency in the thickness direction of the piezoelectric oscillator elements, i.e. the resonance frequency in the direction normal to the substantially spherical shell.

The value of [the resonance frequency in the lateral direction/the resonance frequency in the thickness direction] of the piezoelectric oscillator element can be increased by increasing the value of [the dimension in the thickness direction/the dimension in the lateral direction] of the piezoelectric oscillator element.

The piezoelectric oscillator element of the present invention comprises the piezoelectric body 1 and the pair of electrodes 2 situated in the thickness direction of the piezoelectric body 1.

The piezoelectric material of the piezoelectric body should desirably have a high electromechanical coupling factor and a high dielectric constant. For example, PZT based piezoelectric ceramics, a single crystal such as a solid-solution type single crystal of zinc lead niobate-lead titanate, etc. may be used.

As mentioned above, the shape of the piezoelectric body influences the value of [the resonance frequency in the lateral direction/the resonance frequency in the thickness direction]. Specifically, since a resonance frequency is generally inversely proportional to the thickness of a piezoelectric body, the value of [the dimension in the thickness direction/the dimension in the lateral direction] needs to exceed 1 in order that the value of [the resonance frequency in the lateral direction/the resonance frequency in the thickness direction] may exceed 1. More specifically, when the shape of the piezoelectric body 1 is, for example, columnar, the value of [the height of the column/the diameter of the bottom face] should desirably exceed 1.5. When the shape of the piezoelectric body 1 is a rectangular prism, the value of [the height of the rectangular prism/the longer side of the bottom face] should desirably exceed 1.5.

The piezoelectric oscillator elements can be formed, for example, in the following manner. Conductive thin films serving as electrode faces are formed on the opposed surfaces of the piezoelectric body 1 of a proper size by means of baking of silver, nickel plating, or deposition or sputtering of a desired metal. Then, piezoelectric oscillator elements are separated in a direction perpendicular to the surfaces of the electrodes, and each element is formed in a columnar shape or a polygonal prism shape.

A plurality of oscillator elements thus obtained are arranged in a substantial spherical shell shape. Thereby, the piezoelectric oscillator 102, piezoelectric oscillation plates 3 and piezoelectric oscillator elements of the ultrasonic medical treatment apparatus according to the present invention are formed. By simultaneously applying a voltage to the oscillator elements, ultrasonic energy can be concentrated near the focal point.

It is practical to group the oscillator elements and arrange the piezoelectric oscillation plates 3 of the oscillator elements in a substantial spherical shell shape. Specifically, a plurality of piezoelectric oscillator elements are provided with common electrodes to constitute the piezoelectric oscillation plate. Thereby, it should suffice to connect the common electrodes to the drive circuit only the number of times corresponding to the number of piezoelectric oscillation plates. Thus, the very complex manufacturing step of electrically connecting the drive circuit to the oscillator elements can be simplified.

The piezoelectric oscillation plate 3 can be formed, for example, in the following manner. A plurality of above-mentioned piezoelectric oscillator elements (piezoelectric bodies 1) are arranged on a metallic plate having a desired shape and a thickness of about 50 μm, which will become common electrode 2. The electrodes 2 of the piezoelectric oscillator elements and common electrodes 2 are electrically connected by conductive adhesive or solder. Alternatively, the gaps among the arranged piezoelectric oscillator elements are filled with resin, and then conductive resin is coated over the entire structure to electrically connect the adjacent electrodes.

As a matter of course, the common electrodes may be formed on the piezoelectric body after the piezoelectric bodies are arranged and the resin is filed among the piezoelectric bodies.

In general, the diameter x of the substantially spherical-shell-shaped piezoelectric oscillator 102 needs to be about 300 mm. If the oscillator 102 is formed of a single piezoelectric oscillation plate, the capacitance (several hundred nF) thereof is very high. It is very difficult to provide a drive circuit for applying a pulse voltage (several kV) of high frequency (500 kHz) to the large-capacitance piezoelectric oscillation plate. Thus, it is desired to limit the capacitance to several-ten nF or less. If the dielectric constant of the piezoelectric material and the thickness of the oscillation plate are determined, the limitation to the area of the oscillation plate is determined. It is desirable to combine such piezoelectric oscillation plates in a substantial spherical shell shape and to connect the respective piezoelectric oscillation plates to the drive circuits. In addition, in order to equalize the electric loads to the drive circuits, it is desirable to equally divide the areas of the piezoelectric oscillation plates.

The central portion of the substantially spherical-shell-shaped piezoelectric oscillator 102 may be provided with a hole for attaching an ultrasonic probe for ultrasonic imaging. In this case, since the diameter y of the hole influences the shock wave power obtained by the ultrasonic medical treatment apparatus, the diameter y should desirably be reduced as much as possible. The diameter y of the hole is about 100 mm on the basis of the size of the actually employed probe.

It is desirable that the diameter x of the substantially spherical-shell-shaped piezoelectric oscillator 102 be 150 mm or more and 60 mm or less. If the diameter x is less than 150 mm, the shock wave power obtained from the piezoelectric oscillator 102 cannot be increased enough to break culculi. If the diameter x is greater than 600 mm, the weight of the piezoelectric oscillator 102 and applicator 100 increases, resulting in degradation in operability and an increase in the number of piezoelectric oscillator elements. Consequently, the number of drive power supplies increases and the scale of the system increases.

The ultrasonic radiation surface of the substantially spherical-shell-shaped ultrasonic medical treatment apparatus is provided with an acoustic matching layer for enhancing propagation efficiency of waves through water or a ultrasonic propagation medium. The acoustic matching layer may be formed integrally after the oscillator elements are arranged in a spherical shell shape. However, the acoustic matching layer may be formed for each of separately arranged oscillation plates 3.

According to the piezoelectric oscillator 102 of the ultrasonic medical treatment apparatus of the present invention, a pulse voltage higher than in the prior art can be applied and the power of radiated ultrasonic waves can be greatly increased. If a pulse voltage higher than in the prior art is repeatedly applied to the ultrasonic medical treatment apparatus in which an acoustic matching layer is attached to the surface of conductive resin coated on the entire oscillation plate as common electrode, the acoustic matching layer will be peeled off from the oscillation plate by fatigue failure and the shock wave energy decreases. In the worst case, the generation of shock wave is disabled. The cause of peeling is deficiency in strength of the conductive resin. In order to increase the strength of adhesion at the central portion of the oscillation plate, it is effective to directly bond the adhesive for adhering the acoustic matching layer to a part of the resin filled in the gap among the oscillator elements. In addition, it is desirable not to form a common electrode to the resin portion filled in the gap unless conduction among the oscillator elements is prevented.

As mentioned above, the piezoelectric oscillator element is supplied with an electric pulse and oscillated in the thickness direction thereof to generate ultrasonic pulses. In this case, the oscillator element oscillates in the lateral direction thereof, too. A resonance frequency is present both in the oscillation in the thickness direction and in the oscillation in the lateral direction in accordance with the shape of the oscillator element. The piezoelectric oscillator element used in the conventional ultrasonic medical treatment apparatus has a lower resonance frequency in the lateral direction than in the thickness direction.

The inventors confirmed the following fact. The drive pulse used in the ultrasonic medical treatment apparatus is not a continuous wave pulse and therefore has a relatively wide frequency band. Consequently, even if the pulse for causing oscillation in the thickness direction is applied to the piezoelectric oscillator element, oscillation of a high frequency component in the lateral resonance mode is also caused. Thus, when a high voltage is applied, the oscillation in the thickness direction is combined with the oscillation in the lateral direction and the piezoelectric element is broken by fatigue failure. This fact was confirmed.

In the present invention, resonance of a high frequency component does not occur on the lower frequency side of a basic resonance frequency. Thus, a piezoelectric oscillator element having a higher resonance frequency in the lateral direction than in the thickness direction is used and unnecessary oscillation in the lateral direction is prevented in the vicinity of the resonance frequency in the thickness direction. Thereby, the breaking power of the piezoelectric oscillator element can be increased.

Specific examples will now be described. An experimental model of a piezoelectric oscillation plate was prepared and the characteristics thereof were evaluated. FIG. 6 is a schematic perspective view for illustrating the method of manufacturing this piezoelectric oscillation plate. At first, a ceramic piezoelectric material ("T-96" manufactured by TOSHIBA CERAMICS) having a diameter of 30 mm and a thickness of 3.2 mm was prepared for evaluation of breaking at the time of applying a high-voltage pulse. The basic resonance frequency in the thickness direction of this ceramic material with the thickness of 3.2 mm and a bottom area of 2×2 mm$^2$ is about 500 kHz. Electrodes 2 of based silver, each having a thickness of 5 μm, were formed on opposed surfaces of this ceramic piezoelectric material. The obtained structure was cut in a direction perpendicular to the electrodes in a matrix fashion with a pitch of 2.4 mm by a diamond blade with a thickness of 0.4 mm. As a result, piezoelectric oscillator elements each having a bottom face of 2×2 mm$^2$ were arranged with a pitch of 2.4 mm. In this state of arrangement, epoxy resin was filled among the oscillator elements. Thus, a group of piezoelectric oscillator elements, as shown in FIG. 6, was obtained. Further, in order to attain electrical connection between the cut electrodes 2, a conductive resin layer was coated on the entire surface of the structure. Thus, a piezoelectric oscillation plate was obtained.

FIG. 7 shows the results of measurement of resonance characteristics of the obtained piezoelectric oscillation plate obtained by a measuring device ("4195A" manufactured by Hewlett-Packard). FIG. 7 shows frequency characteristics of impedance of the oscillation plate. Although resonance occurred in the lateral direction of the resin-coupled structure with a diameter of 30 mm in the vicinity of 40 kHz, the level thereof is low. Resonance in the lateral direction of the piezoelectric oscillator element with the bottom face of 2×2 mm$^2$ occurred at 800 kHz. It is found that no resonance occurred in the lateral direction in the vicinity of 500 kHz or a basic resonance frequency in the thickness direction.

A pulse voltage of 500 kHz was applied to this piezoelectric oscillation plate up to 7 kVpp (500 V/mm at 3.2 kVpp). The amplitude of the radiated ultrasonic pulse was great, as compared to the voltage. No variation appeared in the amplitude of the radiated ultrasonic wave even after a pulse voltage of 6 kVpp was applied five million times. Thus, the power of radiated ultrasonic wave was increased.

A second example of the piezoelectric oscillation plate will now be described. In the preceding example, the piezoelectric oscillator elements were completely severed in the thickness direction. In this example, grooves, the depth of which is 70% or more of the thickness, were formed while the oscillator elements were not separated on one side. The grooves were filled with epoxy resin and a common electrode was formed. With this oscillator element, too, the resonance in the lateral direction was greatly reduced, as shown in FIG. 8. Like the preceding example, the ultrasonic power was increased. With this method, the common electrode may be formed on one side only, and the manufacturing steps were simplified.

In the ultrasonic medical treatment apparatus, ultrasonic waves are radiated through water or an ultrasonic propagation medium. Thus, an acoustic matching layer is provided on the ultrasonic radiation surface of the piezoelectric oscillation plate, and the radiation efficiency is enhanced. A two-layer epoxy resin (a first layer of Stycast 2850FT is 1.5 mm thick and a second layer of Epotec 301-2 is 1.2 mm thick) serving as acoustic matching layer was bonded by an epoxy adhesive to the common electrode of the manufactured piezoelectric oscillation plate having a diameter of 30 mm. A pulse voltage was applied to the obtained device and the output characteristics were evaluated. When a pulse of the equal voltage was applied, the sound pressure of radiated ultrasonic wave was about 1.5 times greater than that obtained before the acoustic matching layer was formed. However, when a pulse of 6 kVpp was applied ten thousand times, the acoustic matching layer was peeled from the central portion of the oscillation plate and the sound pressure of the ultrasonic wave decreased greatly. The acoustic matching layer was peeled, with the thickness of the conductive resin layer provided as common electrode on the central part of the device being halved. Thus, the peeling was due to deficiency in strength of the conductive resin.

Figure 10A:
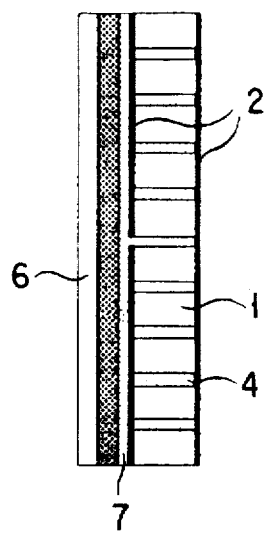
FIG. 10A is a cross-sectional view of a second example of the piezoelectric oscillation plate of the invention.
Figure 10B:
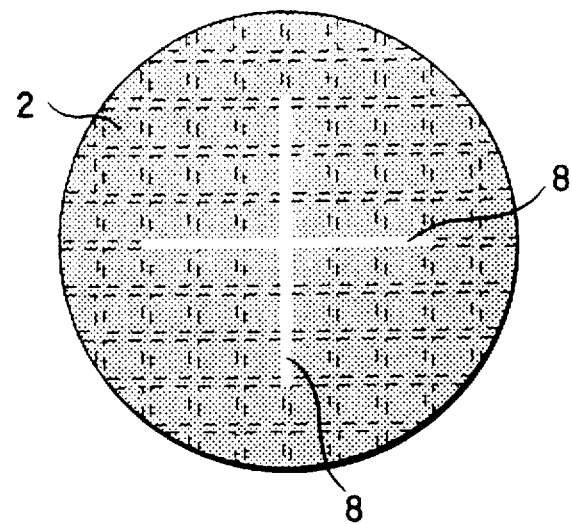
FIG. 10B is a plan view of the second example of the piezoelectric oscillation plate of the invention.
Figure 11:
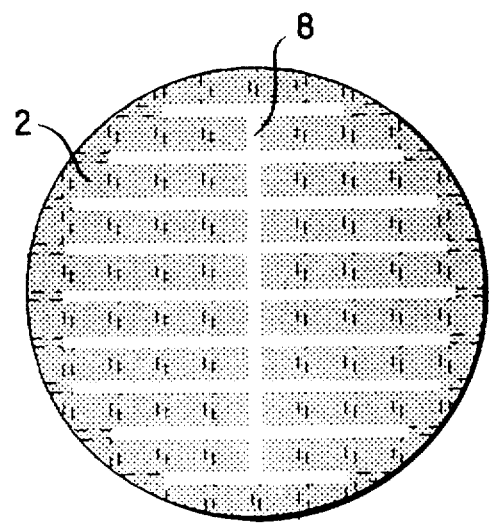
FIG. 11 is a plan view of a third example of the piezoelectric oscillation plate of the invention.

Considering the above, as shown in FIGS. 10A and 10B, the common electrode 2 to be bonded to the acoustic matching layer 6 was not coated on the entire surface of the piezoelectric oscillation plate 3. A part of the resin 4 filled in the gap among the oscillator elements 1 was exposed and bonded directly to the adhesive 7 for adhering the acoustic matching layer 6. FIG. 10A is a vertical cross-sectional view showing the acoustic matching layer 6 bonded to the oscillation plate 3. FIGS. 10B and 11 show examples of a common electrode pattern coated on the oscillation plate 3 shown in FIG. 10A. Since it is sufficient that the common electrode functions to interconnect the electrodes of the piezoelectric oscillator element, the strength of bond is increased advantageously if the exposed region of the filled resin 4 is increased, as shown in FIG. 11. In the case of either common electrode pattern, even if a pulse of 6 kVpp was applied five million times to the oscillation plate on which the acoustic matching layer was bonded, no variation occurred in the amplitude of the radiated ultrasonic wave.

Using the same quality of ceramic as the aforementioned piezoelectric ceramic, the ultrasonic medical treatment apparatus as shown in FIG. 2 was manufactured. In this case, the number of piezoelectric oscillation plates is 16, and these oscillation plates are combined to constitute a spherical shell structure having a diameter of 330 mm, a hole with a diameter of 110 mm, and the radius of curvature of 260 mm. At first, a flat-plate piezoelectric ceramic material corresponding to the 16 divided oscillation plates arranged in a spherical shell shape was cut and separated in a matrix fashion. The grooves among the separated ceramic components were filled with resin, and a common electrode was provided. Thus, the oscillation plates of this invention were obtained. As is shown in FIGS. 10A and 10B, the common electrode on the ultrasonic radiation surface side was formed such that a part of the filled resin was exposed at the central portion (exposed portion 8). The oscillation plates were heated up to a temperature above the glass transition point of the filled resin, pressed on a mold having a predetermined radius of curvature (260 mm), and cooled to room temperature. Thus, 16 divided oscillation plates arranged in a spherical shell shape were obtained. Then, an acoustic matching layer (a first layer of Stycast 2850FT is 1.5 mm thick and a second layer of Epotec 301-2 is 1.2 mm thick) formed in advance with a radius of curvature matching with the surface to be bonded was bonded to the oscillation plates. The obtained 16 vibration plates were arranged in the spherical shell shape. An epoxy resin is filled in the gaps among the oscillator elements. A Teflon-based coating material having a thickness of 50 μm was formed as a moisture-proof film over the entire acoustic matching layer formed in the spherical shell shape.

A lead line for applying a pulse voltage was connected to the electrode of each oscillation plate, and the lead line is connected to each drive power supply.

The manufactured ultrasonic medical treatment apparatus was situated in water and a pulse voltage was applied to each piezoelectric oscillation plate up to 7 kVpp. The sound pressure of shock wave at the focal point was high, as compared to the voltage. The power of shock wave was increased. Even if a pulse voltage of 6 kVpp was applied five million times, no variation occurred in the shock wave sound pressure.

A second example of the manufactured ultrasonic medical treatment apparatus will now be described. In the preceding example, the oscillation plates were formed to have curved surfaces in order to enhance the convergence efficiency. It was possible, however, that flat oscillation plates were combined to constitute a substantially spherical-shell-shaped structure. An acoustic matching layer was bonded to the oscillation plates manufactured such that the piezoelectric oscillator elements were not completely separated, as mentioned above. Thus, the oscillation plates were arranged in a substantial spherical shell shape. Although the convergence efficiency at the focal point was degraded and the maximum sound pressure of shock wave decreased at the focal point, the manufacturing process of the oscillation plates was simplified. By decreasing the area of each flat oscillation plate and providing a great number of such flat oscillation plates, the convergence efficiency was improved. 60 flat oscillation plates with a resonance frequency of 250 kHz were arranged to form a spherical-shell-shaped piezoelectric oscillator, as shown in FIG. 2, etc. With this piezoelectric oscillator, too, the same shock wave as with the preceding piezoelectric oscillator was generated.

Comparative examples will now be described.

In order to perform evaluation of breaking power of the piezoelectric oscillation element at the time of applying a high-voltage pulse, the same ceramic piezoelectric material as used in the embodiment, which has a diameter of 30 mm and a thickness of 4 mm, was prepared (the basic resonance frequency of the aforementioned ceramic material with a thickness of 4 mm and a diameter of the bottom face of 30 mm is 500 kHz). Electrodes of baked silver, each having a thickness of 5 μm, were formed on both opposed surfaces of the ceramic piezoelectric material, thereby obtaining a piezoelectric oscillator element.

FIG. 8 shows resonance characteristics in this case. It is understood, from FIG. 8, that the basic resonance frequency in the lateral direction of this oscillator element is in the vicinity of 70 kHz, that high-frequency resonance appears many times, and that the many spurious radiations occur due to the lateral resonance in the vicinity of 500 kHz or the basic resonance frequency in the thickness direction.

FIG. 9 shows the piezoelectric oscillator element to which 50 thousand pulses of 5 kVpp (625 V/mm) were applied. As shown in FIG. 9, cracks 200 occurred in the piezoelectric oscillator elements 3. If the oscillator element oscillated only in the thickness direction thereof, the internal stress would act to divide the oscillator element into two parts in the thickness direction. It is understood from FIG. 9, however, that the internal stress acts in the radial direction, too.

It is assumed, from the above, that the piezoelectric oscillator element of the comparative example oscillates both in the thickness direction and in the radial direction, and cracks occurred due to synergetic effect of the oscillations in the thickness direction and lateral direction.

According to the present embodiment, as described above, an ultrasonic medical treatment apparatus having a high breaking power and high reliability can be provided.

Another feature of this invention is that the pulse width ($T_1$) of the first negative amplitude, which is greater than the pulse width ($T_0$) corresponding to the resonance frequency of the piezoelectric oscillation plate and piezoelectric oscillator element, is set in the piezoelectric oscillation plate and piezoelectric oscillator element.

The inventors found that the shock wave energy can be increased with the same applied voltage by a method of applying a pulse voltage, i.e. by controlling the pulse width.

Figure 1A:
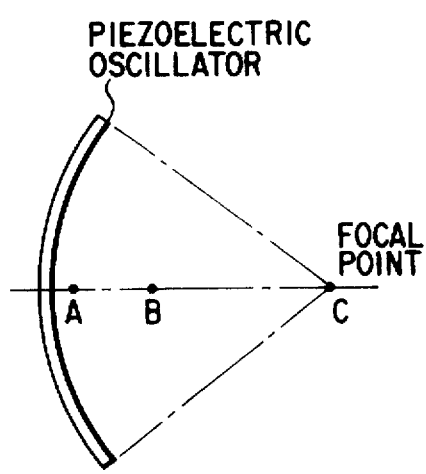
FIGS. 1A and 1B are conceptual views for illustrating how ultrasonic waves are converted to a shock wave.
Figure 1B:
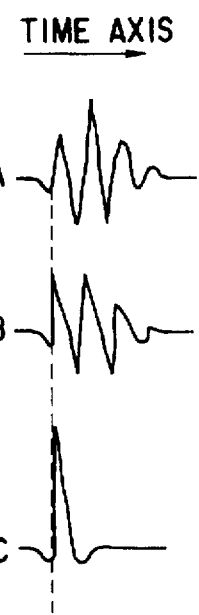

This will now be described in greater detail. FIGS. 12A and 12B show examples of a drive pulse waveform and a radiated ultrasonic waveform. Since a hydrophone might be destroyed by measuring shock waves, a flat type small experimental element with a diameter of 30 mm was used as oscillation plate and radiated ultrasonic waves were measured by a needle type hydrophone manufactured by IMO-TEC. Since the amplitude was small, the radiated waves were not shock waves but had a waveform equivalent to that of ultrasonic waves near the surface, radiated from a large-area oscillation plate. Although the oscillation pulse should desirably have one cycle of sine wave, it is difficult in fact to obtain such an oscillation pulse, as shown in FIGS. 12A and 12B. A disturbance appears in the latter portion of the waveform, following the positive amplitude. In addition, as shown in FIGS. 1A and 1B, the portion of the amplitude of the radiated ultrasonic pulse waveform, which is converted to the shock wave, is only the first positive amplitude portion. Moreover, only one wavelength from the first negative amplitude to the positive amplitude of the drive waveform component relates to the first positive amplitude waveform of the ultrasonic pulse.

The power of breaking culculi is proportional to the shock wave energy. The sock wave energy is expressed by a value obtained by integrating the amplitude on the basis of the time axis and space axis. Since the spatial distribution of the shock wave depends on the converging means, the shock wave depending on the drive waveform has a time-axis waveform as shown in FIG. 1B. The greater the maximum amplitude of the shock wave waveform shown in FIG. 1B and the greater the width of the zero-cross pulse, the greater the shock wave energy. Accordingly, it is desirable to increase the amplitude p of the first positive amplitude of the ultrasonic pulse radiated from the oscillation plate and the pulse width $T_2$.

In general, the piezoelectric oscillation plate is driven at the resonance frequency thereof. Specifically, the pulse width of the applied pulse voltage corresponds to the resonance frequency. However, the inventors found by researches that when the oscillation plate is driven by a single waveform transiting from a negative-amplitude pulse voltage to A positive-amplitude pulse voltage, the conversion efficiency to the shock wave energy becomes greater if a frequency lower than the resonance frequency is used. It is difficult to realize a single pulse voltage of several kV order, and in fact a disturbance occurs in the waveform following the negative-amplitude voltage. However, it is considered that the width ($T_1$) of the first negative amplitude is substantially equivalent to the frequency of the pulse voltage. It was confirmed that the ultrasonic sound pressure produced by the piezoelectric oscillation number is increased by driving the piezoelectric oscillation plate with a voltage of a frequency lower than the resonance frequency ($T_1 > T_0$).

The above effect is obtained by making $T_1$ greater than $T_0$, but this effect becomes more conspicuous by adopting the value of $1.1 \times T_0$ or more. If $T_1$ is too great, a departure from the resonance frequency is large and the oscillation efficiency lowers. Thus, it is preferable to adopt the value of about $1.4 \times T_0$ or less. More preferably, $T_1$ should be $1.2 \times T_0$ to $1.3 \times T_0$.

The drive pulse is generally applied from an LC resonance circuit for releasing an electric charge accumulated in a capacitor. The value $T_1$ can easily be varied by properly setting the value of L, etc.

Specific examples of the present invention will now be described. In order to study the optimal drive condition for shock wave generation, an oscillator was prepared wherein an acoustic matching layer is formed on an ultrasonic radiation surface of piezoelectric ceramic material with $\phi$ 30 mm and 500 kHz. FIG. 13 shows an equivalent circuit of the drive circuit (drive power supply). In FIG. 2, this drive circuit is included in the treatment apparatus body 110. The drive circuit comprises a DC power supply VH, a resistor R, inductances Lp and Ls, and a high withstand voltage switching device SW.

In this drive circuit, the pulse width of the oscillation pulse was controlled by adjusting the values of the inductances Lp and Ls connected in series/parallel to the oscillator element. FIG. 14 shows the drive pulse width dependency of T-96 material manufactured by Toshiba Ceramics) used as piezoelectric ceramic material. White circles indicate the relationship between $T_1$ and p, and black circles indicate the relationship between $T_2$ and p. The resonance frequency of the single oscillator element is 515 kHz, and the pulse width T0 calculated from this value is 0.97 μsec. When the pulse width $T_1$ of the first negative amplitude of the drive pulse was varied in the range of 0.8 to 1.7 μsec, the value $T_1$ at the time the first positive amplitude p of the radiated ultrasonic waveform takes the maximum value was 1.25 μsec. On the other hand, the pulse width $T_2$ of the radiated ultrasonic wave tended to be proportional to $T_1$, but the width of variation was small. Even when the drive pulse width $T_1$ was considerably varied, the pulse width $T_2$ of the radiated ultrasonic wave oscillates and remains near the resonance frequency. From FIG. 14, it is understood that the optimal drive pulse width $T_1$ was 1.3 μsec and the sound pressure was maximum. This value is 1.34 times greater than the pulse width $T_0$ calculated from the resonance frequency of the oscillator element. The pulse width $T_2$ of the radiated ultrasonic wave at this time was 1 μsec and substantially equal to $T_0$.

Under the above drive conditions, a shock wave generating apparatus was actually manufactured, and shock waves were produced.

A plurality of piezoelectric oscillator elements were arranged in a spherical shell shape having a radius of curvature of 260 mm, a hole with an inside diameter of 110 mm, and an outer dimension of 330 mm. The number of arranged piezoelectric oscillator elements was 24, and the respective oscillator elements had substantially equal areas. The thickness of each piezoelectric oscillator element was adjusted to have a resonance frequency of 500 kHz. An acoustic matching layer was formed on the ultrasonic radiation surface of each piezoelectric oscillation element, and an ultrasonic probe for observing culculi was attached in the central hole and contained in a water bag with a bellows. A drive pulse of $T_1=1.3$ μsec was applied to this shock wave generating apparatus.

For the purpose of comparison, the same apparatus was driven by a pulse of $T_1=1.0$ μsec.

The shock wave energy in the case of $T_1=1.3$ μsec was about 20% greater than in the case of $T_1=1.0$ μsec.

The piezoelectric ceramic material used for shock wave generation should desirably have a high electro-mechanical coupling factor kt, which represents an electromechanical energy conversion efficiency, and a high dielectric constant which permits input of large electric energy.

The catalog value of the aforementioned T-96 material is kt - 51% and the dielectric constant is 2000. However, the actual measurement using an oscillator element with $\phi$ 30 mm showed that kt=45% and dielectric constant=1800. Since there are several kinds of materials having a substantially equal kt and different dielectric constants, the drive pulse width dependency of other piezoelectric ceramic materials were examined. The selected piezoelectric materials are T-43 and T99 of Toshiba Ceramics and C-7 of Fuji Ceramics. Table 1 shows the catalog values and actual values of kt and dielectric constant of the respective materials. The values in parentheses () are actual values.

TABLE 1

| Piezoelectric Material | kt (%) | Dielectric Constant | Resonance Frequency (kHz) |
| --- | --- | --- | --- |
| T-96 | 51 (45) | 2000 (1800) | (515) |
| T-43 | 47 (38) | 1230 (1800) | (515) |
| T-99 | 50 (41) | 3200 (1800) | (525) |
| C-7 | 49 (42) | 3900 ± 400 (4300) | (520) |

Figure 16:
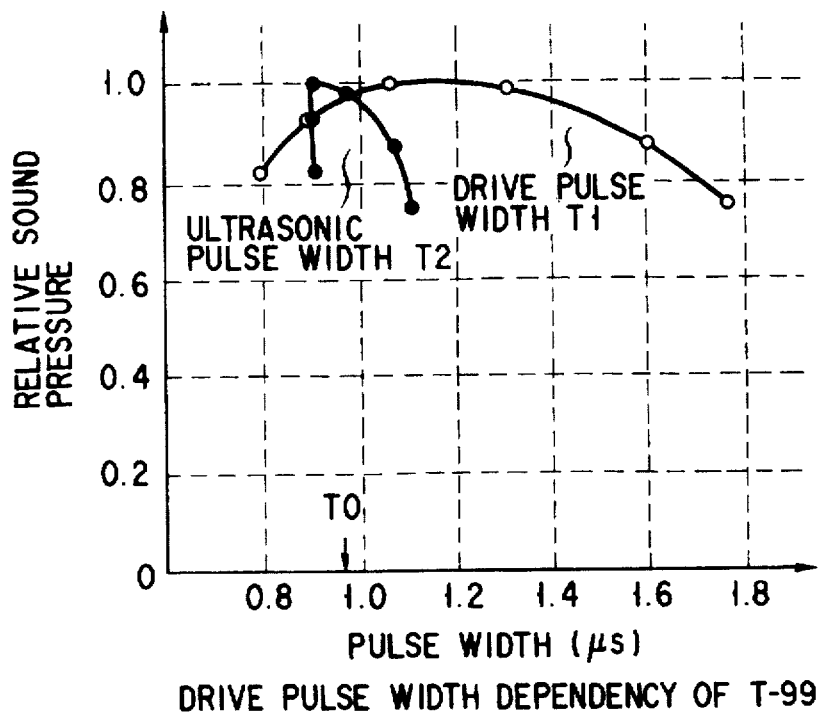
Figure 17:
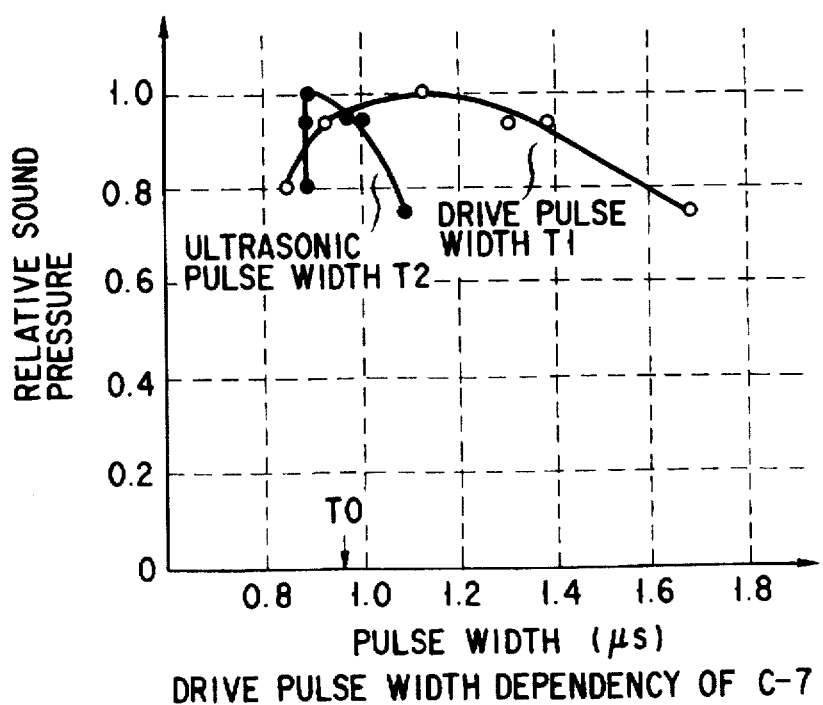

FIGS. 15 to 17 shows the pulse width dependency of each oscillator element. The resonance frequency of each single oscillator element is 515 to 520 kHz, and the pulse width $T_0$ calculated from this value is 0.96 to 0.97 μsec. Table 2 shows optimal drive pulse widths $T_1$ with maximum shock wave energy, which are understood from the FIGURES.

TABLE 2

| Piezoelectric Material | $T_0$ (μsec) | $T_1$ (μsec) | $T_2$ (μsec) | $T_1/T_0$ | $T_2/T_1$ |
| --- | --- | --- | --- | --- | --- |
| T-96 | 0.97 | 1.3 | 1.0 | 1.34 | 1.3 |
| T-43 | 0.97 | 1.3 | 0.95 | 1.24 | 1.26 |
| T-99 | 0.96 | 1.3 | 0.95 | 1.35 | 1.37 |
| C-7 | 0.96 | 1.2 | 0.9 | 1.25 | 1.33 |

Figure 18:
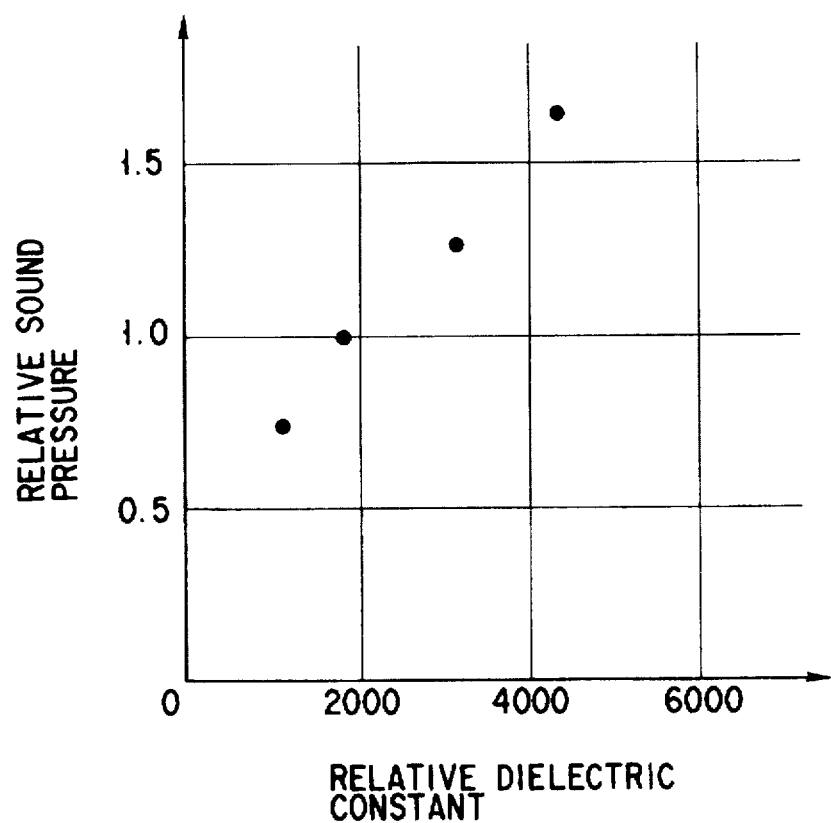
FIG. 18 is a graph showing the relationship between a relative sound pressure and a relative dielectric constant.

FIG. 18 shows the dielectric constant dependency characteristics of the first positive voltage peak p of the ultrasonic pulse radiated when an equal voltage is applied to each oscillator element under the optimal drive conditions. Using the p value of T-96 material as a standard value, the actually measured dielectric constant of each piezoelectric material is plotted. There is a tendency that the peak sound pressure of shock wave becomes higher as the piezoelectric material has a higher dielectric constant. However, since the amplitude of the radiated ultrasonic is proportional to the drive voltage, the material having a higher dielectric constant is not necessarily better. The applied voltage is limited by the mechanical strength and insulation strength, and the output voltage is limited on the drive circuit side, too. Thus, the optimal piezoelectric material must be selected from the standpoint of all aspects.

The pulse width dependency of the drive pulse was also examined with respect to the piezoelectric oscillation plate, as shown in FIG. 6, wherein a number of piezoelectric oscillator elements, each having a columnar shape and a higher resonance frequency in the lateral direction than in the thickness direction, are integrally arranged. With this structure of the piezoelectric oscillation plate, it is possible to enhance the durability of the piezoelectric oscillation plate to fatigue failure due to repeated application of high-voltage drive pulses to the piezoelectric oscillation plate.

A piezoelectric ceramic material of T-96 with a thickness of 2.8 mm and φ 30 mm was cut by a diamond cutter in a matrix fashion with a pitch of 2 mm and divided into piezoelectric element groups each having a size of about 1.7 mm. Then, epoxy resin was filled in grooves among the cut piezoelectric elements. The upper and lower surfaces of the integrated oscillation plate were coated with a conductive adhesive and the electrodes on the upper and lower surfaces of the piezoelectric elements were commonly connected. The resonance frequency of this oscillator was 535 kHz. The drive pulse width dependency of the oscillator having the acoustic matching layer on the ultrasonic radiation surface was examined. As a result, the optimal drive pulse width $T_1$ was 1.1 μsec, which was 1.18 times greater than the pulse width $T_0$ (0.93 μsec) calculated from the resonance frequency of the single element, like the piezoelectric ceramic oscillator. The pulse width $T_2$ of the radiated ultrasonic was 0.9 μsec, and $T_1/T_2$ was 1.22 like the piezoelectric ceramic material.

The resonance frequency of the piezoelectric oscillator was also examined. The frequency was varied to about 200 kHz. It is optimal that the drive pulse width (negative pulse $T_1$) is about 1.2 times greater than the pulse width calculated from the resonance frequency of the single element, like the case of 500 kHz.

The shock wave generating apparatus has a structure, for example, as shown in FIG. 2. In the above embodiment, the evaluation of characteristics was made based on the ultrasonic pulse. Needless to say, the characteristics of the ultrasonic pulse correspond to those of the shock wave.

As has been described above, according to the present invention, the first positive pulse amplitude of the radiated ultrasonic wave can be increased by setting the pulse width of the first negative amplitude of the drive pulse of the piezoelectric oscillation plate to be greater than the pulse width of the resonance frequency of the piezoelectric oscillation plate. Therefore, the shock wave energy converted from this ultrasonic wave can be increased.

This advantage can also be obtained in the case where a plurality of oscillator elements are bonded to one another by resin, as shown in FIG. 5.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic medical treatment apparatus comprising:
   a piezoelectric oscillation plate including a plurality of piezoelectric oscillator elements, said elements each having a higher resonance frequency in a lateral direction thereof than in a thickness direction thereof; and
   a drive unit for supplying a drive voltage to each of said piezoelectric oscillator elements,
   wherein said piezoelectric oscillation plate has a ultrasonic radiation surface, and further includes a acoustic matching layer, a resin is filled in gaps among said elements and an adhesive for adhering the acoustic matching layer to the ultrasonic radiation surface is directly bonded to only a portion of said resin in a central region of said piezoelectric oscillation plate.

2. The ultrasonic medical treatment apparatus according to claim 1, wherein said drive unit includes a drive power supply for applying a high-voltage pulse of at least 500 V/mm to said piezoelectric oscillator elements.

3. The ultrasonic medical treatment apparatus according to claim 1, wherein each of said piezoelectric oscillator elements has a resonance frequency in the lateral direction thereof, which is at least 1.5 times greater than a resonance frequency in the thickness direction thereof.

4. The ultrasonic medical treatment apparatus according to claim 1, wherein said plurality of piezoelectric oscillator elements constitute a piezoelectric oscillation plate.

5. The ultrasonic medical treatment apparatus according to claim 1, wherein said plurality of piezoelectric oscillator elements are bonded to each another by resin.

6. The ultrasonic medical treatment apparatus according to claim 1, wherein said plurality of said piezoelectric oscillation plates constitute a substantially spherical-shell-shaped piezoelectric oscillator.

7. The ultrasonic medical treatment apparatus according to claim 6, wherein each of said piezoelectric said plurality of piezoelectric oscillation plates which have an acoustic matching layer is provided on ultrasonic radiation surfaces of said piezoelectric oscillation plates.

8. The ultrasonic medical treatment apparatus according to claim 1, wherein each of said piezoelectric oscillation plates has an equal area and an acoustic matching layer, said piezoelectric oscillation plates are constituted a substantial spherical shell shape, and said acoustic matching layer is provided on ultrasonic radiation surfaces of said piezoelectric oscillation plate.

9. The ultrasonic medical treatment apparatus according to claim 4, wherein said piezoelectric oscillation plate comprises a plurality of small oscillator elements, a resin is filled in gaps among said small oscillator elements, and an adhesive for adhering said acoustic matching layer to said ultrasonic radiation surface is directly bonded to part of said resin in a central region of said piezoelectric oscillation plate.

10. The ultrasonic medical treatment apparatus according to claim 1, wherein said drive unit includes means for supplying to said piezoelectric oscillation plate a drive voltage having a pulse width ($T_1$) of a first negative amplitude, which is greater than a pulse width ($T_0$) corresponding to the resonance frequency of said piezoelectric oscillation plate.

11. The ultrasonic medical treatment apparatus according to claim 10, wherein said $T_1$ and $T_0$ meet the relationship,
$1.1 \times T_0 \leq T_1 \leq 1.4 T_0$.

12. An ultrasound medical treatment method for providing ultrasonic treatment to a patient, comprising the steps of:
   providing a piezoelectric oscillation member; and
   supplying a drive voltage to said piezoelectric oscillation member wherein said drive voltage has a pulse width (T1) of a first negative amplitude, which is greater than a pulse width (T0) corresponding to a resonance frequency of said piezoelectric oscillation member to thereby provide ultrasound energy having an increased shock wave energy being applied to said patient.

13. The ultrasonic medical treatment method according to claim 12, wherein said $T_1$ and $T_0$ meet the relationship,
$1.1 \times T_0 \leq T_1 \leq 1.4 T_0$.

14. The ultrasonic medical treatment method according to claim 12, wherein said piezoelectric oscillation member includes a plurality of piezoelectric oscillator elements.

15. The ultrasonic medical treatment method according to claim 14, including the step of bonding said plurality of piezoelectric oscillator elements to each other by a resin.

16. The ultrasonic medical treatment method according to claim 12, wherein said plurality of said piezoelectric oscillation member forms a substantial portion of a spherical-shell-shaped piezoelectric oscillator.

17. The ultrasonic medical treatment method according to claim 12, further including the step of providing an acoustic matching layer on ultrasonic radiation surfaces of said piezoelectric oscillation member.

18. The ultrasonic medical treatment method according to claim 12, including the step of arranging said piezoelectric oscillation member in a substantial spherical shell shape and providing an acoustic matching layer on an ultrasonic radiation surface of said piezoelectric oscillation member.

* * * * *